United States Patent
Garcia-Cardena et al.

(10) Patent No.: US 10,232,336 B2
(45) Date of Patent: Mar. 19, 2019

(54) SYSTEMS AND METHOD FOR HIGH-THROUGHPUT TESTING

(71) Applicants: The Charles Stark Draper Laboratory, Inc., Cambridge, MA (US); The Brigham and Women's Hospital, Inc., Boston, MA (US)

(72) Inventors: Guillermo Garcia-Cardena, Cambridge, MA (US); Peter Mack, Chapel Hill, NC (US); Jeffrey T. Borenstein, Newton, MA (US); Ahmad S. Khalil, Boston, MA (US); Eli J. Weinberg, Needham, MA (US); Jason O. Fiering, Boston, MA (US); Ernest S. Kim, Cambridge, MA (US); William J. Adams, Jr., Cambridge, MA (US); Mitchell Hansberry, Southborough, MA (US); Stephen Bellio, Newton, MA (US)

(73) Assignees: The Charles Stark Draper Laboratory, Inc., Cambridge, MA (US); The Brigham and Women's Hospital, Inc., Boston, MA (US)

( * ) Notice: Subject to any disclaimer, the term of this patent is extended or adjusted under 35 U.S.C. 154(b) by 945 days.

(21) Appl. No.: 14/534,898

(22) Filed: Nov. 6, 2014

(65) Prior Publication Data
US 2015/0126411 A1 May 7, 2015

Related U.S. Application Data

(60) Provisional application No. 61/900,652, filed on Nov. 6, 2013.

(51) Int. Cl.
*G01N 1/00* (2006.01)
*G01N 1/18* (2006.01)
(Continued)

(52) U.S. Cl.
CPC .......... *B01J 19/0046* (2013.01); *C12M 23/12* (2013.01); *C12M 35/04* (2013.01); *B01J 2219/00587* (2013.01)

(58) Field of Classification Search
CPC .................................. G01N 1/00; G01N 1/18
(Continued)

(56) References Cited

U.S. PATENT DOCUMENTS

| 5,055,263 A | 10/1991 | Meltzer |
| 6,116,099 A | 9/2000 | Carl |

(Continued)

FOREIGN PATENT DOCUMENTS

| DE | 38 36 654 A1 | 5/1989 |
| WO | WO-2010/083282 A1 | 7/2010 |

OTHER PUBLICATIONS

Blackman et al. "A New In Vitro Model to Evaluate Differential Responses of Endothelial Cells Simulated Arterial Shear Stress Waveforms," Journal of Biomechanical Engineering, vol. 124, Aug. 2002, pp. 397-407.

(Continued)

*Primary Examiner* — Brian J. Sines
(74) *Attorney, Agent, or Firm* — Hamilton, Brook, Smith & Reynolds, P.C.

(57) ABSTRACT

The systems and methods described herein relate to a high-throughput flow apparatus. The apparatus is used with an array of wells, and is configured to impart a predetermined shear stress on cells cultured within each of the wells of the array of wells. The apparatus includes a plurality of mechanical tips. The plurality of mechanical tips each includes a head with a hemispheroid shape. The apparatus also includes a motor associated with at least one of plurality (Continued)

of mechanical tips. The motor is configured to drive the plurality of mechanical tips to impart the shear stress pattern in each of the wells.

14 Claims, 18 Drawing Sheets

(51) Int. Cl.
    *B01J 19/00*     (2006.01)
    *C12M 1/32*     (2006.01)
    *C12M 1/42*     (2006.01)

(58) Field of Classification Search
    USPC ............ 422/68.1; 436/43, 63, 174, 175, 177
    See application file for complete search history.

(56) References Cited

U.S. PATENT DOCUMENTS

| | | | |
|---|---|---|---|
| 6,655,194 B2* | 12/2003 | Hajduk | G01N 3/24 |
| | | | 73/54.37 |
| 6,769,292 B2* | 8/2004 | Mansky | G01N 11/04 |
| | | | 506/12 |
| 7,482,169 B2 | 1/2009 | Gjerde et al. | |
| 8,460,622 B2 | 6/2013 | Motadel | |
| 8,652,835 B2* | 2/2014 | Link | C12M 45/02 |
| | | | 210/198.2 |
| 9,006,149 B2 | 4/2015 | Garcia-Cadena et al. | |
| 2004/0123650 A1 | 7/2004 | Kolosov et al. | |
| 2004/0131500 A1 | 7/2004 | Chow | |
| 2005/0032200 A1* | 2/2005 | Sun | C12M 35/04 |
| | | | 435/286.7 |
| 2005/0202566 A1 | 9/2005 | Frojmovic | |
| 2006/0068492 A1* | 3/2006 | Choi | C12M 23/08 |
| | | | 435/293.2 |
| 2006/0223049 A1 | 10/2006 | Dancu et al. | |
| 2008/0038816 A1 | 2/2008 | Ting et al. | |
| 2012/0171364 A1* | 7/2012 | Haider | H01L 27/20 |
| | | | 427/100 |
| 2013/0337500 A1* | 12/2013 | Tan | G01N 33/5005 |
| | | | 435/39 |
| 2016/0024454 A1* | 1/2016 | Sniadecki | G01N 33/5302 |
| | | | 435/288.7 |

OTHER PUBLICATIONS

Dai et al. "Distinct Endothelial Phenotypes Evoked by Arterial Waveforms Derived from Artherosclerosis Susceptible and Resistant Regions of Human Vasculature," PNAS, vol. 101, No. 41, Oct. 12, 2004, pp. 14871-14876.
International Search Report for PCT Application No. PCT/US2010/021002, dated Jun. 18, 2010, 4 pages.
U.S. Office Action in U.S. Appl. No. 12/687,717 dated Mar. 15, 2011.
U.S. Office Action in U.S. Appl. No. 12/687,717 dated Nov. 17, 2011.
U.S. Office Action in U.S. Appl. No. 12/687,717 dated Apr. 7, 2014.
U.S. Office Action in U.S. Appl. No. 12/687,717 dated Jul. 16, 2012.
U.S. Office Action in U.S. Appl. No. 12/687,717 dated Sep. 3, 2013.
Written Opinion for PCT Application No. PCT/US2010/021002, dated Jun. 18, 2010, 4 pages.
U.S. Appl. No. 12/687,717, filed Jan. 14, 2010.
International Search Report and Written Opinion dated Feb. 13, 2015 in PCT Application No. PCT/US2014/064339.
U.S. Notice of Allowance in U.S. Appl. No. 12/687,717 dated Dec. 15, 2014.
Xu, J., et al., "Cell, GPR68 Senses Flow and Is Essential for Vascular Physiology," Cell, 173-762-775 (2018).

* cited by examiner

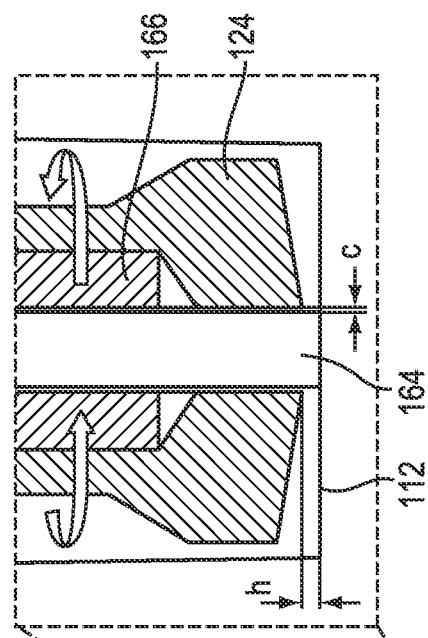
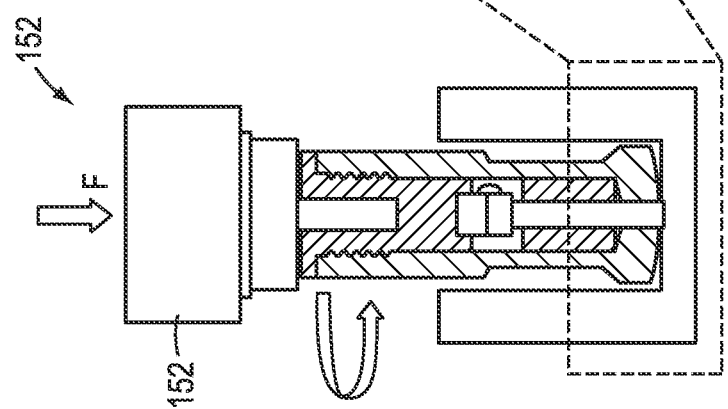
FIG. 4C
FIG. 4D

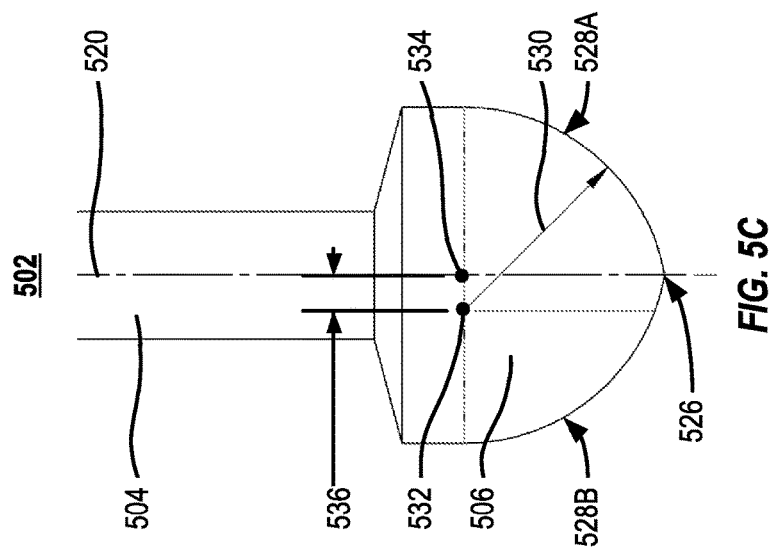
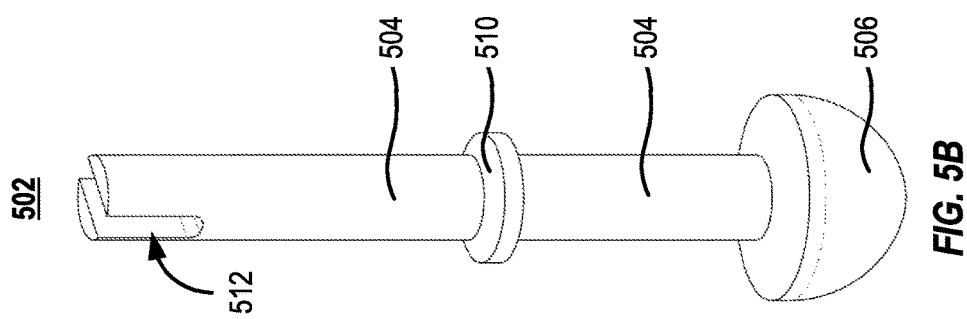

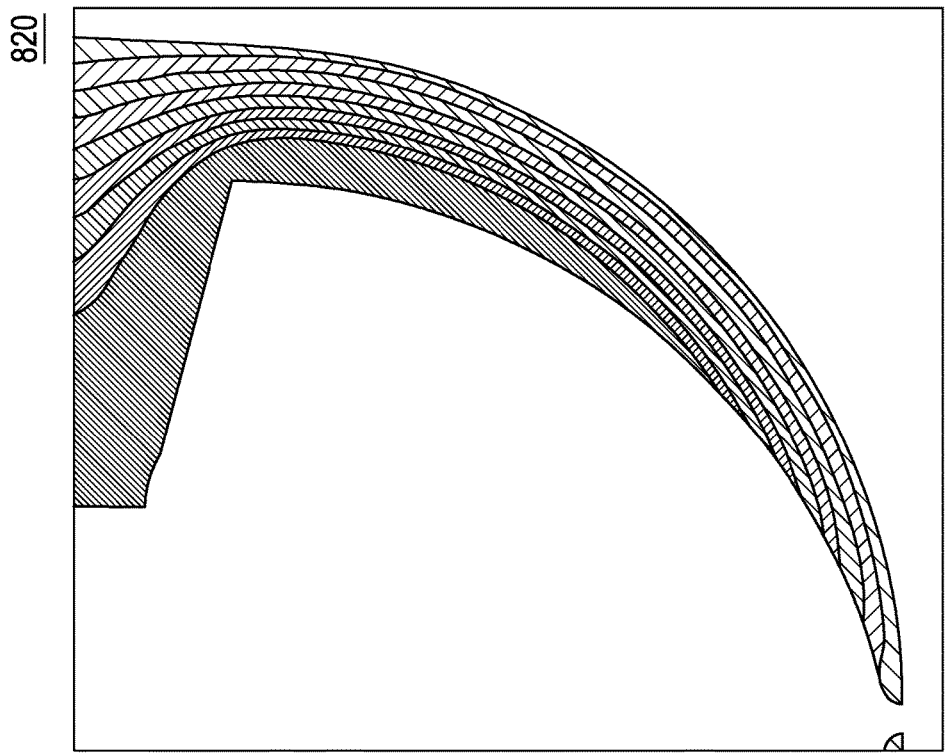
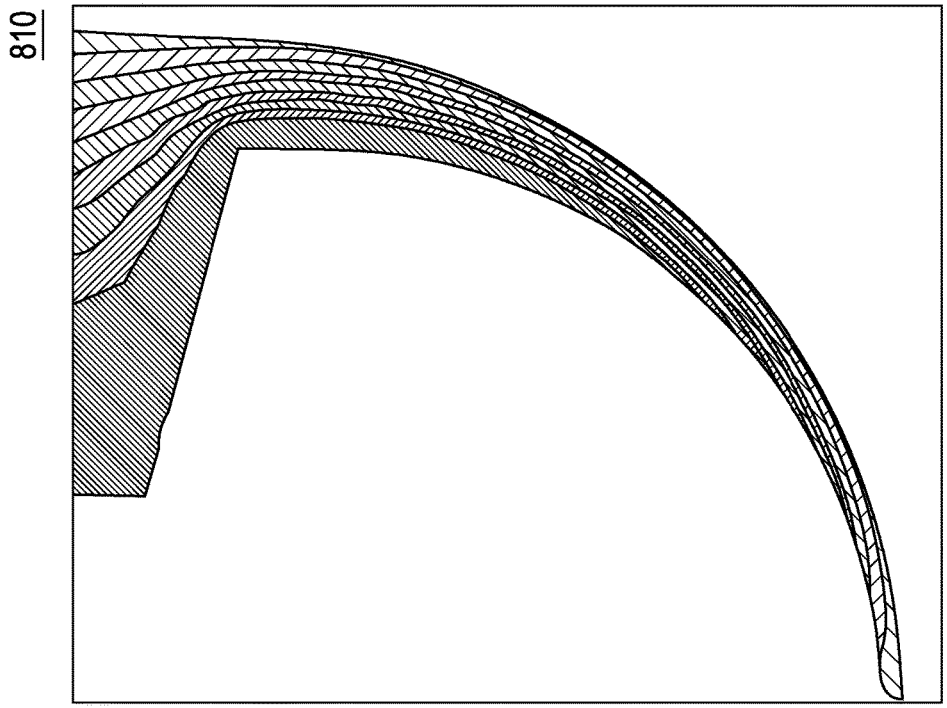

SYSTEMS AND METHOD FOR HIGH-THROUGHPUT TESTING

REFERENCE TO RELATED PATENT APPLICATIONS

This application claims priority to and the benefit of U.S. Provisional Patent Application No. 61/900,652, filed on Nov. 6, 2013, which is herein incorporated by reference in its entirety.

BACKGROUND OF THE DISCLOSURE

Drug discovery can include biological testing of candidate compounds by exposing the candidate compounds to samples of tissue that exhibit the disorder to be treated. For example, in screening candidate compounds for efficacy against atherosclerosis, endothelial cells can be exposed to a shear stress, which affects the growth and behavior of adherent cultured cells. In some implementations, the cultured cells react more like in vivo cells when a shear stress (also referred to as shear force) that mimics in vivo conditions is applied to the cultured cells.

SUMMARY OF THE DISCLOSURE

According to one aspect of the disclosure, a system for inducing shear within an array of wells includes a plurality of mechanical tips. The plurality of mechanical tips each include a head with a hemispheroid shape. The plurality of mechanical tips also each correspond to a different well of the array of wells. The system also includes a motor associated with at least one of plurality of mechanical tips. The motor is configured to drive the at least one of the plurality of mechanical tips to impart a shear stress pattern in the well corresponding to the at least one of the plurality of mechanical tips.

In some implementations, the head of each of the plurality of mechanical tips includes a pinpoint standoff. The pinpoint standoff maintains a predetermined distance between a bottom of the head of each of the plurality of mechanical tips and a floor of its corresponding well. The hemispheroid shape has a cross-sectional shape defined by two adjacent arcs, where the center of each arc is a predetermined distance from a midline of the cross-sectional shape. The hemispheroid shape can form a point about which the head of each of the plurality of mechanical tips rotates. In some implementations, the hemispheroid shape has a semi-circular cross-sectional shape. In some implementations, each of the plurality of mechanical tips includes a collar to maintain a predetermined distance between the head of each of the plurality of mechanical tips and a floor of its corresponding well.

In some implementations, the system includes the array of wells, and each well of the array of wells have a hemispherical bottom. An arc of a cross-sectional shape of the head can be defined by the equation $(R)^2 = (x + R \sin \Phi)^2 + (y)^2$, where R is a radius of the arc and $\Phi$ is a tilt angle.

In some implementations, each of the plurality of mechanical tips each include a groove that enables the mechanical tip to move vertically relative to the motor.

According to another aspect of the disclosure, a method includes providing a system for inducing shear and an array of hemi-spherical bottomed wells. The system for inducing shear includes a plurality of mechanical tips. The plurality of mechanical tips each include a head with a hemispheroid shape. The system also includes at least one motor associated with the plurality of mechanical tips. The method includes disposing the head of each of the plurality of mechanical tips into each well of the array of wells, and rotating the head of each of the plurality of mechanical tips with the at least one motor to generate a shear force within the each well of the array of wells.

In some implementations, the method includes culturing a field of cells in each well of the array of wells. The induced shear force is substantially constant across the field of cells in each well of the array of wells. In some implementations, the head of each of the plurality of mechanical tips includes a pinpoint standoff. The pinpoint standoff maintains a predetermined distance between a floor of each head and a floor of its corresponding well.

In some implementations, the hemispheroid shape includes a cross-sectional shape defined by two adjacent arcs, where the center of each arc is a predetermined distance from a midline of the cross-sectional shape. The hemispheroid shape forms a point about which the head of each of the plurality of mechanical tips rotates. In some implementations, the semi-spheroid shape has a semi-circular cross-sectional shape.

In some implementations, each of the plurality of mechanical tips includes a collar to maintain a predetermined distance between the head of each of the plurality of mechanical tips and a floor of its corresponding well. In some implementations, an arc of a cross-sectional shape of the head can be defined by the equation $(R)^2 = (x + R \sin \Phi)^2 + (y)^2$, where R is a radius of the arc and $\Phi$ is a tilt angle.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various implementations of the present disclosure are described with reference to the following drawings, in which:

FIG. 4C illustrates a schematic cutaway view of an mini-shear machine as shown in FIG. 4B.

FIG. 4D illustrates an enlarged schematic cutaway view of a portion of the mini-shear machine shown in FIG. 4C.

FIG. 5B illustrates a perspective view of a tip removed from the mini-shear machines illustrated in FIG. 5A.

FIG. 5C illustrates a cross-sectional view of the head from FIG. 5B.

FIGS. 11A-11C illustrate simulated velocity profiles generated in wells using mechanical tips with different shaped heads.

DETAILED DESCRIPTION OF THE DISCLOSURE

The present disclosure describes unit structures known as mini-shear machines ("MSMs") that are configured to create predetermined shear stress within each of an array of wells. For example, the wells may each be a single well of a multi-well plate, or may instead be an array of discrete wells—e.g., miniature cuvettes in a rack. MSMs include tips associated with each of the wells of the array of wells. Motors, individually or commutatively, rotate the tips within each of the wells to generate the predetermined shear force.

Figure 1:
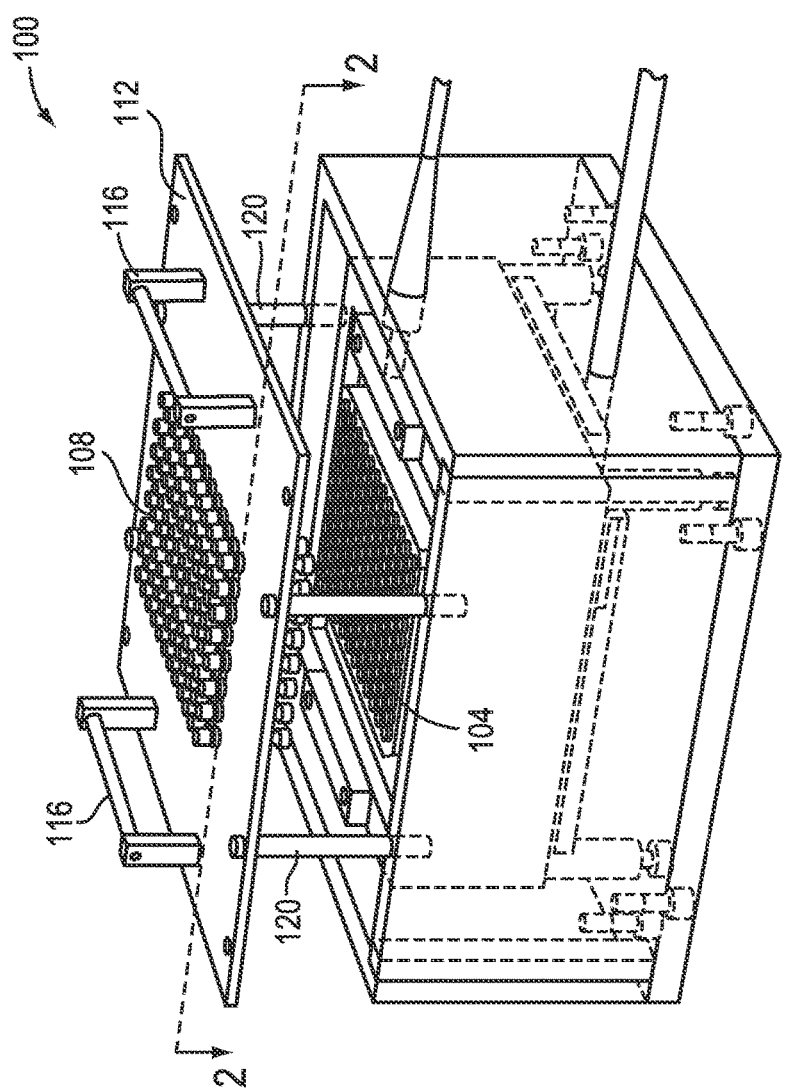
FIG. 1 illustrates an example high-throughput flow system.

In various implementations, the present disclosure relates to high-throughput biological screening. FIG. 1 illustrates an example high-throughput flow system 100. As illustrated, the high-throughput flow system 100 includes an array of wells 104 and an array of mechanical tips 108. As further described below with respect to FIG. 3, each mechanical tip 108 may in fact be part of, and be controlled by, a larger MSM. Each mechanical tip 108 corresponds to one of the wells 104. More specifically, an interface 112 is coupled to the array of tips 108 and is employed to position each tip 108 within its corresponding well 104. For example, the interface 112 may be, as illustrated, a single motor plate. In some implementations, the single motor plate 112 is machined from stainless steel to give a high-precision flatness. A pair of handles 116 may be employed to lower and raise the single motor plate 112, and guide posts 120 may be employed to steer the plate 112 and facilitate proper alignment with the wells 104 and tips 108.

Figure 2:
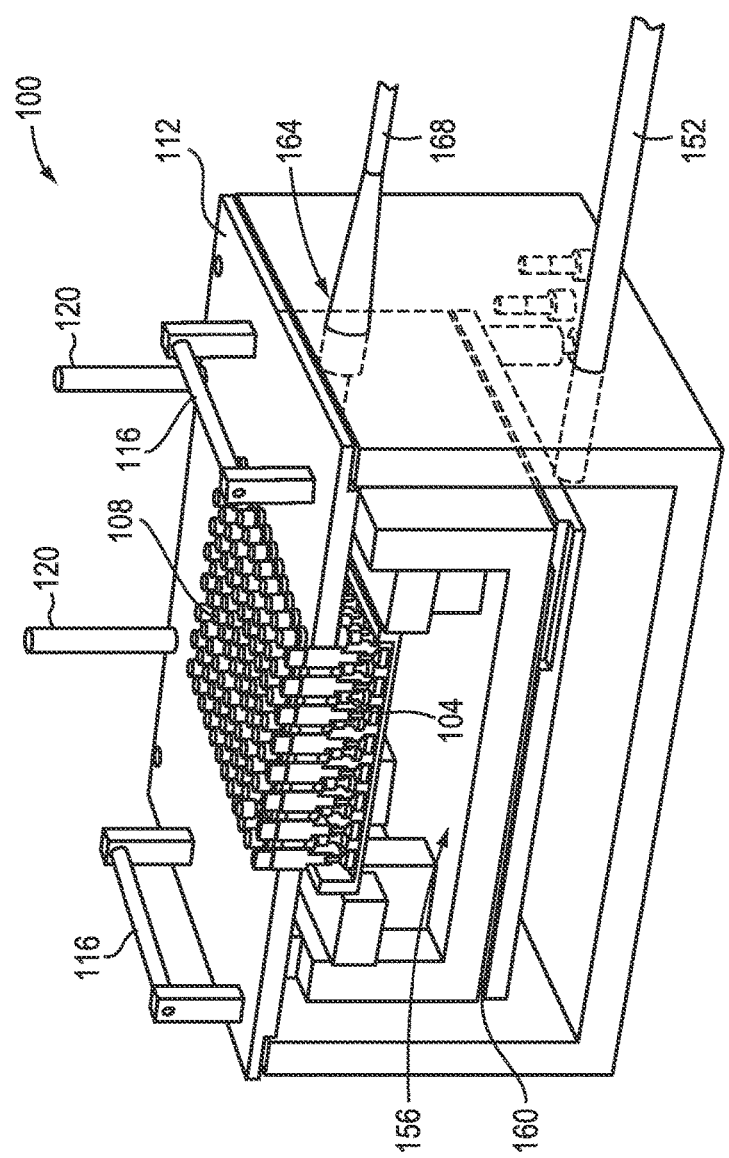
FIG. 2 illustrates a cutaway view of the high-throughput flow system of FIG. 1, along the line 2-2.

FIG. 2 illustrates a cross-sectional view of the example high-throughput flow system 100 illustrated in FIG. 1. As illustrated in FIG. 2, the motor plate 112 is clamped down to simultaneously seat each of the tips 108 within its corresponding well 104. By machining the motor plate 112 and coupling the motor plate 112 to the array of mechanical tips 108, the tips 108 may be raised or lowered in unison as to be precisely located at the same height within the tip's corresponding well 104. In some implementations, the height of each of the tips 108 within the tip's corresponding well 104 is individually controllable. In this way, each tip 108 may be actuated, as further described below, to impart substantially the same shear stress pattern to cells within each well 104. Individually controlling the height of each tip 108 can enable the high-throughput flow system 100 to accommodate for variations in the depths of each of the wells 104. As such, replicates of the same shear stress pattern may be studied in parallel, vastly reducing the overall experiment time.

In some implementations, the array of wells 104 is defined within a well plate. For example, 96 individual wells 104 may be individually formed (e.g., machined) within the well plate. Any number of wells 104 may be formed within the well plate. For example, a multi-well configuration of 6, 12, 24, 48, 96, 384, or 1536 wells may be employed. The well plate may be, for example, any of the commercially available well plates manufactured by Nunc, a division of Thermo Fisher Scientific, Inc. In addition, microfluidic channels may optionally be employed to address any one or more of the individual wells 104 to facilitate the introduction therein of cells, cell culture medium, and/or test compounds (e.g., candidate drugs, small molecules, and/or genes), as further described below.

Figure 8:
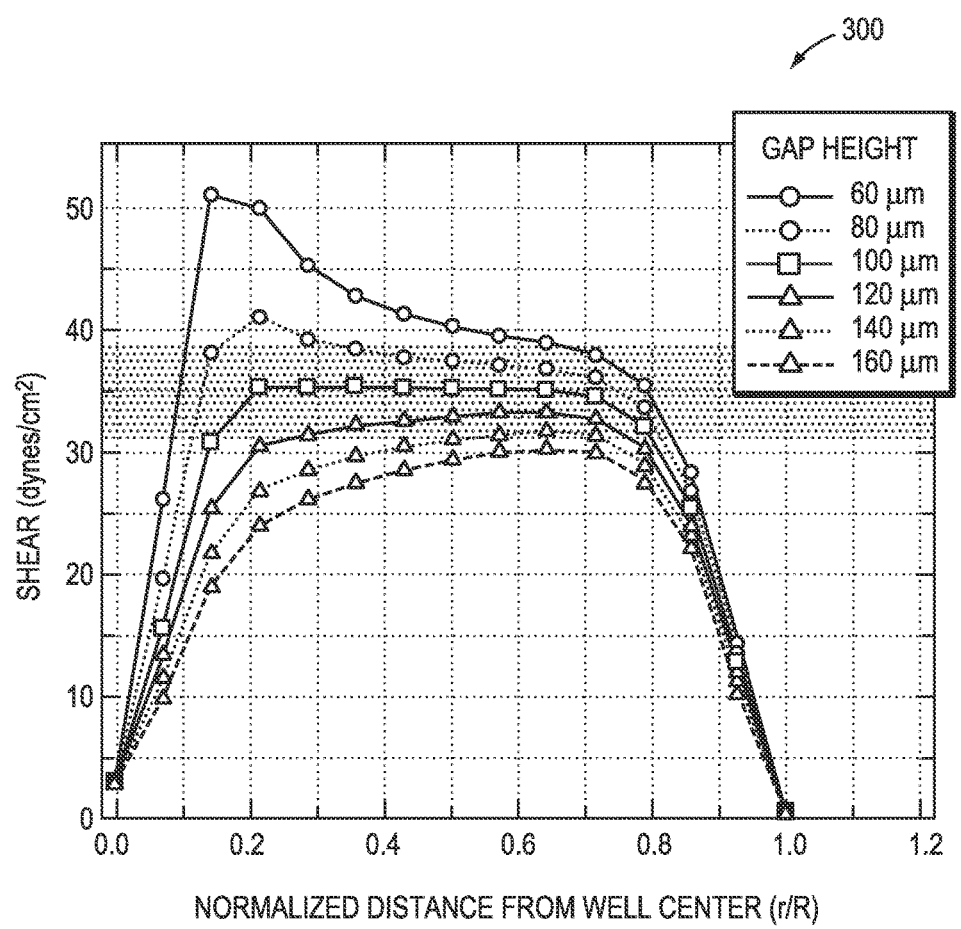
FIG. 8 illustrates a graph of the shear distributions on the well surface depicted in FIG. 3 for various gap heights between the illustrated rotatable head and well surface.

In some implementations, as further described below with reference to FIG. 8, each tip 108 is actuated to impart, within its corresponding well 104, a shear stress pattern that mimics a waveform—e.g., a physiological hemodynamic waveform—present in the circulatory system of an organism, such as a human or mouse. In other implementations, the tip 108 is configured to impart a shear stress pattern that mimics a waveform present in the renal system of an organism. In some implementations, the waveforms may be atheroprotective waveforms, atheroprone waveforms, and/or waveforms that increase or direct the differentiation of cells, e.g., stem cells. Exposing the cells to the shear stress generated by one of the tips 108 enables the behavior of the cells and/or test compounds to be investigated under different flow conditions. Each shear stress pattern may include temporal and spatial variations. For example, the shear stress patterns may be oscillatory shear stress patterns. In some implementations, the shear stress patterns are steady shear stress patterns. For example, the shear stress pattern can be a constant shear pattern over the course of the experiment.

Figure 3:
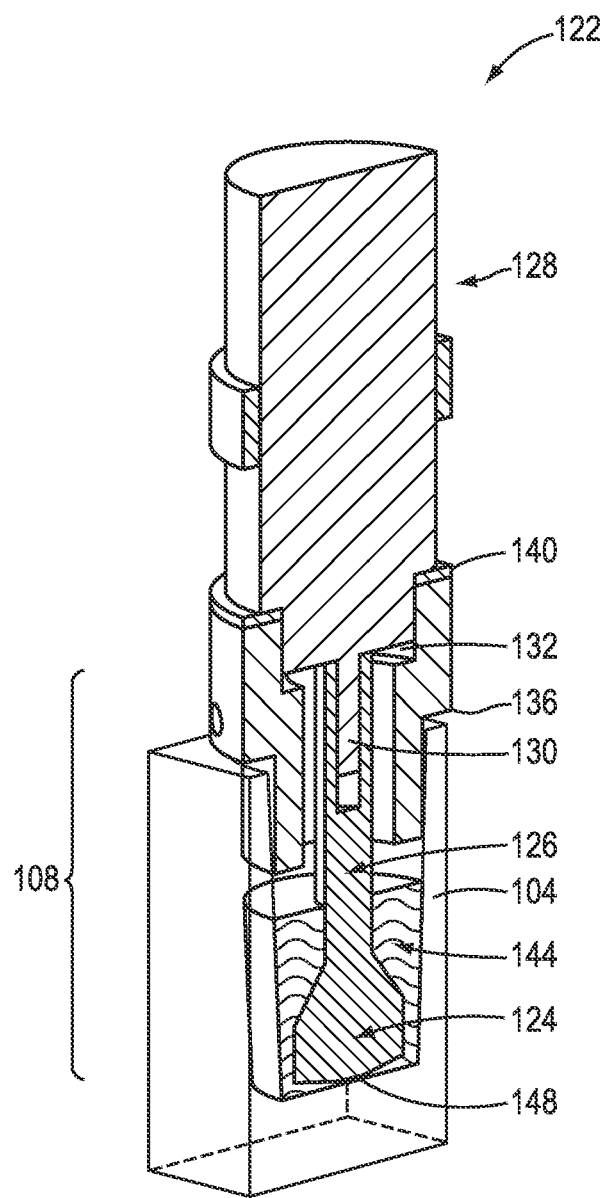
FIG. 3 illustrates a cutaway view of a single example mini-shear machine for use with the high-throughput flow system of FIG. 1.

FIG. 3 illustrates a cross-sectional view of a mechanical tip 108 as part of a larger MSM 122. As illustrated, the tip 108 may include a rotatable head 124 and an elongate shaft 126 that extends therefrom. The shaft 126 couples to a motor 128 (e.g., a variable-speed precision motor, such as a stepper motor) of the MSM 122. A motor collar 136 aligns the motor 128 with the well 104. In some implementations, the tip 108 is coupled to a motor shaft 130 by close-slip fit and glue. One or more shim washers 132 are placed on the motor axis between the motor 128 and tip 108. The number and thickness of the washers 132 controls the axial position of the tip 108 relative to the floor of the well 104. In some implementations, the washers 132 include a wax. The system 100 may be heated such that the wax melts, enabling the bottom tip of the head 124 to come into contact with the floor of the well 104. When the wax solidifies, the wax enables the bottom tip of the head 124 to make contact with the floor of the well 104, without drilling into the floor of the well as the tip 108 rotates. Tip 108 position may be monitored during assembly using either physical tools, such as a drop tester, or optical tools.

Using these high-precision techniques for fixing the axial position of the tip 108, and because shear-distribution simulations (discussed below with reference to FIG. 7) provide a guide for the sensitivity of shear errors with tip 108 height, it is possible to compensate for slight imprecision in well 104 depths of common well plates, and subsequently place bounds on the total margin of error.

In some implementations, by fixing the axial position of the tip 108, the head 124 (and elongate shaft 126) may be positioned so as not to contact a surface of its corresponding well 104 or any of the biological cells cultured therein. In other implementations, the head 124 may in fact be allowed to touch a bottom of the corresponding well 104. For example, as described below in relation to FIG. 5D, the tip 108 includes a standoff that maintains a predetermined distance between the floor of the well 104 and the head 124.

In some implementations, with reference still to FIG. 3, the motor collar 136, which may screw onto motor threads, acts as an adapter so that the MSM 122 sits snugly in its corresponding well 104. Above the collar 136, the motor plate 112 couples to the motor 128. Pushing the motor plate 112 down, as described above, seats the collar 136 onto the well 104. In some implementations, a gasket 140 is placed between the collar 136 and the motor plate 112 to ensure that the collar 136 is pushed flush against the top of the well plate when the motor plate 112 is lowered. Controlling the axial position of the tip 108 relative to the collar 136, and pushing the collar 136 securely against the well plate together ensure that the distance between the head 124 of the tip 108 and the surfaces of the well 104 is controlled.

In some implementations, the MSM 122 is designed to interface with an existing well plate, such as a 96-well plate manufactured by Nunc. In some implementations, the well plates incorporate physical features to secure the radial and axial positions of the head 124 to maintain radial, and optical alignment marks to monitor head position.

In some implementations, hemodynamic shear stress waveforms are applied within all the wells 104 in a well plate by arraying one MSM 122 for each well 104. In general, there is one motor 128, tip 108, and collar 136 for each well 104. In other implementations, a motor 128 drives a plurality of tips 108. For example, fewer motors 128 may be used with mechanical linkages, such as pulleys or chains, so that each motor 128 drives multiple heads 124 in parallel. The heads 124 may alternatively be driven by non-mechanical methods, including electromagnetic or pneumatic actuation. The high-throughput flow system 100 can be adapted to accommodate a wide variety of commercially available well plates, custom-built well plates, and well plates with different dimensions and numbers of wells 104.

Figure 4A:
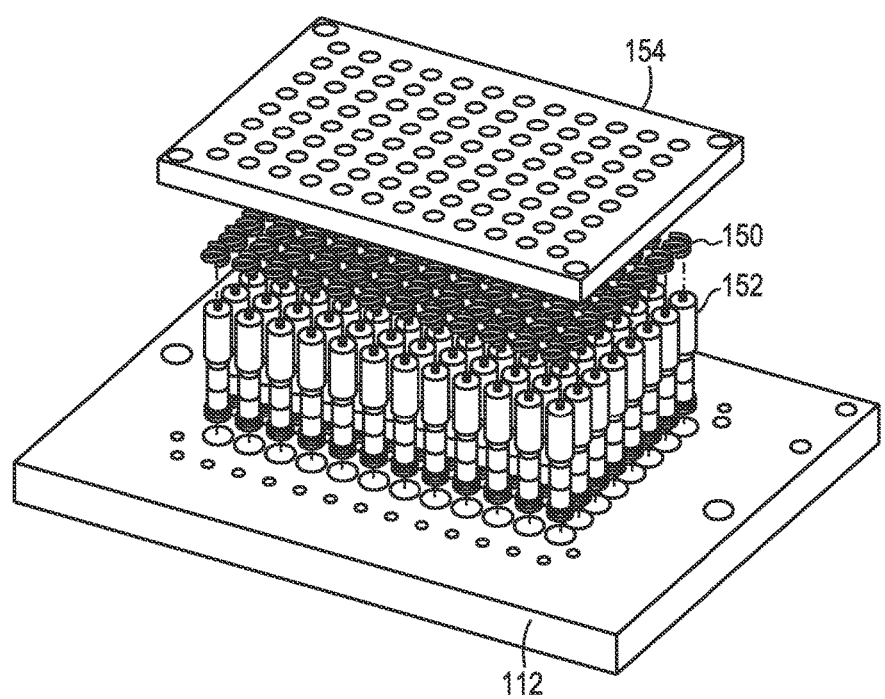
FIG. 4A illustrates an exploded view of an example mini-shear machine array for use with the high-throughput flow system of FIG. 1.
Figure 4B:
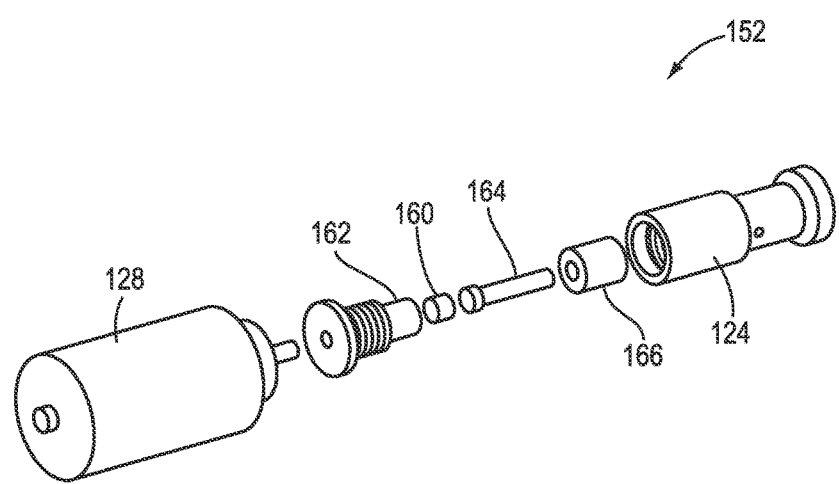
FIG. 4B illustrates an exploded view of the mini-shear machine as shown in FIG. 4A.

The shear stress pattern delivered to the biological cells adhered to the well bottom 104 is dependent on the distance, h, between the rotating head 124 of the tip 108 and the bottom of the wells 104 of the well plate. Given typical dimensions of the device and the hemodynamic settings in which the tip 108 may be used, a 1 µm error in h may produce a 1% error in the shear stress applied. To enforce an exact and consistent distance h, a post (also referred to as a standoff) of precise length may be incorporated to the MSM as illustrated in FIGS. 4A-4D or into the head as illustrated in FIG. 5D. With reference to FIG. 4A, a spring 150 is disposed over each of the MSMs 152, and a spring plate 154 urges the springs 150 against the tops of MSMs 152. As shown in FIG. 4B, each of the MSMs 152 includes a motor 128, a jewel bearing 160 between a shaft seat 162 (which receives the shaft of motor 128) and the post 164. The head 124 is secured (e.g., via threads) to the shaft seat 162, and the post 164 passes through a TEFLON bearing 166 and the head 124. With reference to FIGS. 4C and 4D, the spring associated with MSM 152 urges the post 164 (via the motor 128, shaft seat 162 and bearing 160) against the floor of the corresponding well in plate 112. This enforces the desired distance h, which is established by the extension of the post 164 beyond the bottom of the head 124. In some implementations, a clearance space c separates the inner wall of the head 124 from the post 164 to permit free rotation of the head around the post; similarly, jewel bearing 160 facilitates free rotation of the shaft seat 162 (and, hence, the head 124) relative to the top of the post 164. This self-adjusting configuration maintains a constant distance between head and well bottom despite variations in commercially available well plates. Furthermore, the floor of each well have a small recess to receive the post 164 therein in order to enforce radial alignment (e.g., concentricity) between the head 124 and the well wall; in this case, the post 164 has extra length corresponding to the depth of the recess.

In another implementation, a precise and accurate distance h is achieved by attaching a precision-machined sleeve to the outer body of each motor and spring loading the motors so the bottom edge of each sleeve is held against the floor of the corresponding well. Each head rotates within its surrounding sleeve, and the distance between the bottom of the head and the bottom of the sleeve is h. When the sleeve rests against the bottom of the well, it captures a portion of the well volume. The cells cultured within this sleeve experience uniform shear according to their radial position and are not subject to concentricity error because the inner walls of the sleeve define the boundary of the rotating flow. Outside the sleeve, in the excess medium between the sleeve and the well wall, no cells are cultured and no measurements made. The sleeves may, for example, be machined from glass to enable aggressive cleaning procedures and to ensure biocompatibility. Glass also provides relatively low thermal conductivity to resist transfer of heat from motors to the cultured cells. Using this configuration, each head will automatically adjust to the desired distance h above the well bottom to within, for example, ±5 µm. Additionally, the sleeve defines new sidewalls in the well, such that the sleeves are concentric to within, for example, 2% of the well diameter.

Figure 5A:
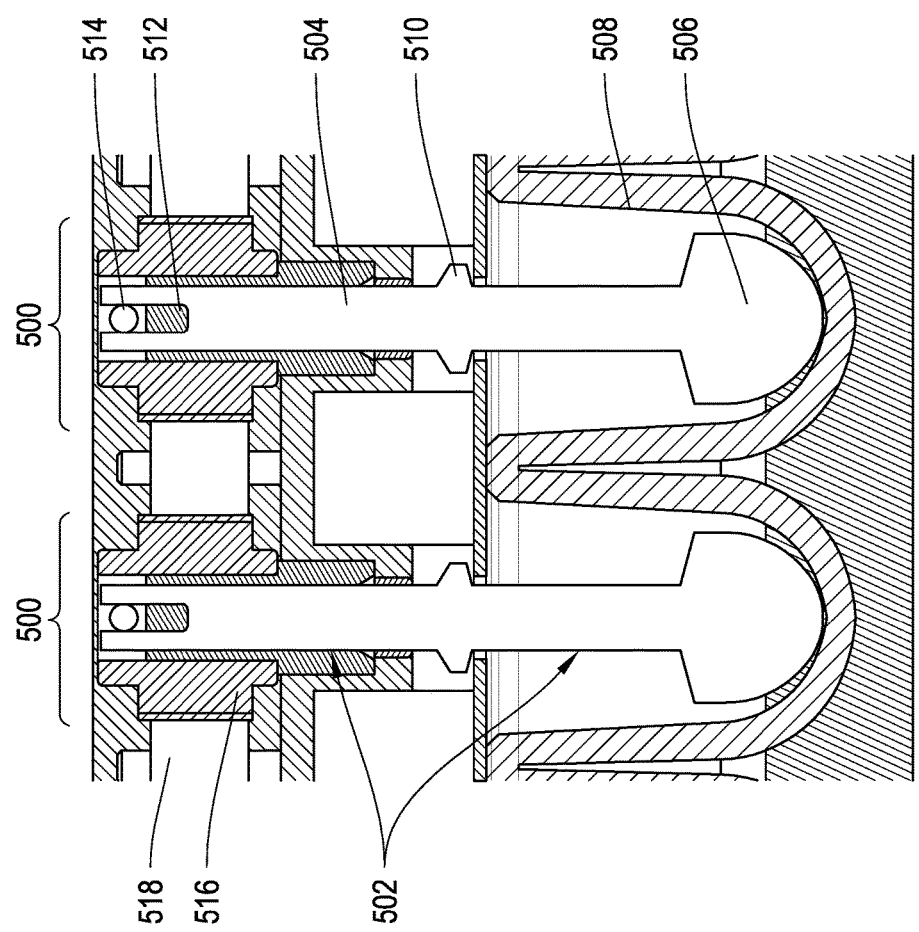
FIG. 5A illustrates a schematic cross-sectional view of example mini-shear machines for use in the high-throughput flow system of FIG. 1.
Figure 5D:
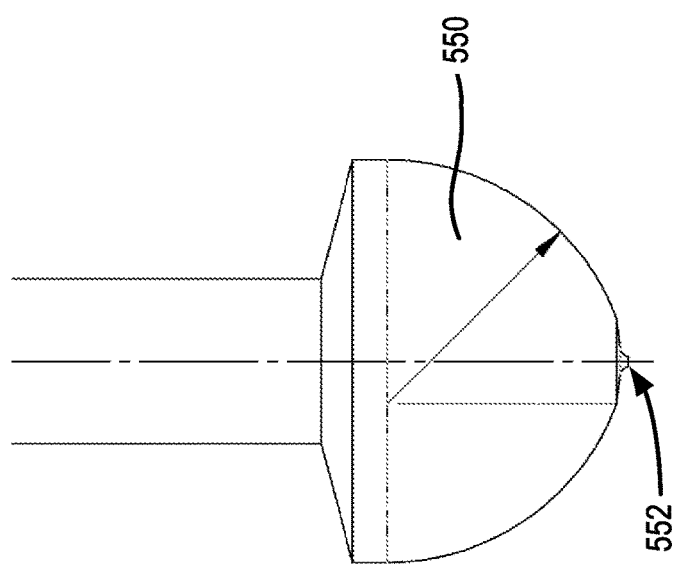
FIG. 5D illustrates a cross-section of an example head for use with the example mini-shear machines shown in FIG. 5A.

FIG. 5A illustrates a schematic cross-sectional view of an example MSMs 500 for use in the high-throughput flow system of FIG. 1. As described above in relation to FIG. 3, each MSM 500 includes a tip 502. The tip 502 includes a shaft 504 and a head 506. The head 506 is configured to fit into a well 508 with a rounded (or semi-circular) bottom. The shaft 504 also includes a collar 510 to maintain a predetermined position of the head 506 within the well 508. At the end of the tip 502 opposite the head 506, the tip 502 includes a groove 512. The groove 512 is configured to receive a drive pin 514. The drive pin 514 is coupled to a gear 516. The teeth of the gear 516 engage a drive belt 518. The drive belt 518 rotates the gear 516, which in turn rotates the tip 502. The depth of the groove 512, being deeper than the diameter of the drive pin 514, enables the tip 502 to move vertically relative to a drive pin 514. As described herein, the head 506 can be vertically (or axially) positioned at different distances from the floor of the well 508 depending on predetermined scientific needs.

FIG. 5B illustrates a perspective view of a tip 502 removed from the MSMs 500 illustrated in FIG. 5A. As described above, the tip 502 includes a vertical shaft 504. A head 506 is coupled to the first end of the shaft 504. The end of the shaft 504 opposite the head 506 includes a groove 512 configured to receive a drive pin. The shaft 504 also includes a collar 510.

The shaft 504 and the head 506 are manufactured from stainless steel, titanium, gold, aluminum, a polymer, or a combination thereof. In some implementations, the shaft 504 and the head 506 are manufactured form the same materials and in other implementations the shaft 504 and the head 506 are manufactured from different materials. In some implementations, an outer surface of the head 506 is coated with a biocompatible material. For example, the head 506 can be manufactured from aluminum and then coated in gold, titanium, a ceramic, or a polymer.

The shaft 504 includes an outer diameter between about 0.05 inches and about 0.2 inches, between about 0.06 inches and about 0.15 inches, between about 0.07 inches and about 0.12 inches, or between about 0.07 inches and about 0.1 inches. A length of the shaft 504 is between about 0.5 inches and about 1.25 inches, between about 0.5 inches and about 1.0 inches, or between about 0.25 and about 0.75 inches. In some implementations, the size of the shaft 504, the head 506, and the tip 502 is determined responsive to the size of the well with which the tip 502 is to be used. For example, the above sizes may be employed when the system 100 is used in combination with a 96 well plate. In some implementations, the size of the components of the tip 502 is scaled according to the size of the well. For example, a 6 well plate includes wells that are larger in diameter when compared to the wells of a 96 well plate. Accordingly, a tip that is used in combination with a 6 well plate may be larger than a tip used with a 96 well plate. The relationship between the size of the tip and the size of the well is described further in relation to FIG. 5E.

The groove 512 is configured to receive the drive pin 514. The groove 512 is wider than the outer diameter of the drive pin 514 such that a loose fit can occur between the drive pin 514 and the groove 512. In some implementations, the groove 512 is between about 0.1 inches and about 0.01 inches wide, between about 0.08 inches and about 0.01 inches wide, between about 0.06 inches and about 0.02 inches wide, or between about 0.05 and about 0.03 inches wide. In some implementations, the groove 512 is between about 0.15 inches and about 0.05 inches deep, between about 0.14 inches and about 0.06 inches deep, or between about 0.14 inches and about 0.07 inches deep. The head 506 is illustrated in greater detail in relation to FIGS. 5C-5E.

FIG. 5C illustrates a cross-sectional view of the head 506 from FIG. 5B. As described above, the head 506 is coupled to the shaft 504. The tip 502 rotates about the axis 520. The head 506, in some implementations, is hemispherical. In other implementations, the head 506 includes non-spherical hemispheroid shapes. For example, the cross-sectional shape of the hemispheroid head 506 can be a prolated semi-oval, a semi-vesica piscis, or a semi-almond shape. As illustrated in FIG. 5C, the head 506 of the tip 502 has a hemispheroid shape with a semi-vesica piscis cross-sectional shape, and forms a point 526 at the axis 520. In a hemispheroid configuration, the cross-sectional shape of the head 506 includes two adjacent arcs 528a and 528b (generally referred to as arcs 528). Each arc 528 has a radius 530, and the center 532 of the circle that would be formed by the arc 528 (also referred to as the center of the arc 528) is shifted from the origin 534 by a predetermined distance 536. Shifting the center of the arc 528a to the left of the axis 520 and the center of the arc 528b to the right of the axis 520 forms the point 526.

FIG. 5D illustrates a cross-section of an example head 550. The head 550 includes a hemispheroid shaped. The head 550 includes a pinpoint standoff 552. In some implementations, the pinpoint standoff 552 of the head 550 is formed by forming a relief cut about the point of the head 550. In some implementations, the pinpoint standoff 552 maintains a predetermined distance between the head 550 and the floor of a well. The pinpoint standoff 552 can reduce the area of the head 550 that makes contact with the floor of a well and reduce the damage the rotation of the head 550 causes to the cells cultured within the well. In some implementations, the pinpoint standoff 552 is between about 0.005 inches and about 0.01 inches, between about 0.005 inches and about 0.008 inches, or between about 0.005 inches and about 0.006 inches.

Figure 5E:
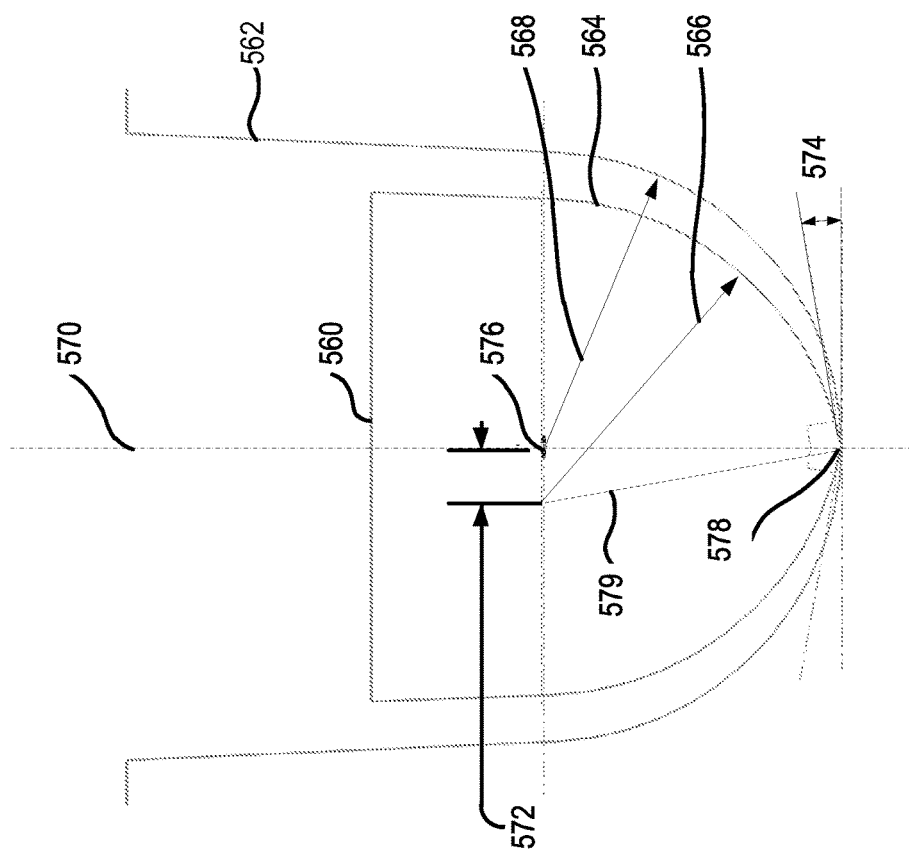
FIG. 5E illustrates a cross-sectional view of an example head within a well.

FIG. 5E illustrates a cross-sectional view of an example head 560 within a well 562. The head 560 has a hemispheroid shape. The cross-section of the head 560 forms an arc 564. The arc 564 has a radius 566. The well 562 has a radius 568. The center of the circle formed by the arc 564 is shifted from the axis 570 by a predetermined distance 572. A tilt angle 574 determines the distance the center of the circle formed by the arc 564 is shifted from the axis 570. In some implementations, the tilt angle 574 is selected such that the distance between the arc 564 and the well 562 linearly increases when moving from the point 578 that the head 560 make contact with the well 562 to end of the arc 564.

In some implementations, the shape of the head 560 is configured respective to the shape of the well. For example, the head 560 is configured to generate a constant shear stress over a field of cells cultured on the interior wall of the well 560. In the example illustrated in FIG. 5E, if the radius 568 of the well is r, the radius 566 of the head 560 is R, and the tilt angle 574 is Φ. The tilt angle Φ is the angle between a horizontal tangent line at the point 578 and a line tangent to line 579. The predetermined distance 572 is approximately −r(tan Φ), and r=R(cos Φ). The equation for the arc 564 is:

$$(R)^2 = (x + R \sin \Phi)^2 + (y)^2$$

wherein the x and y axes are centered at the origin 576.

Figure 6:
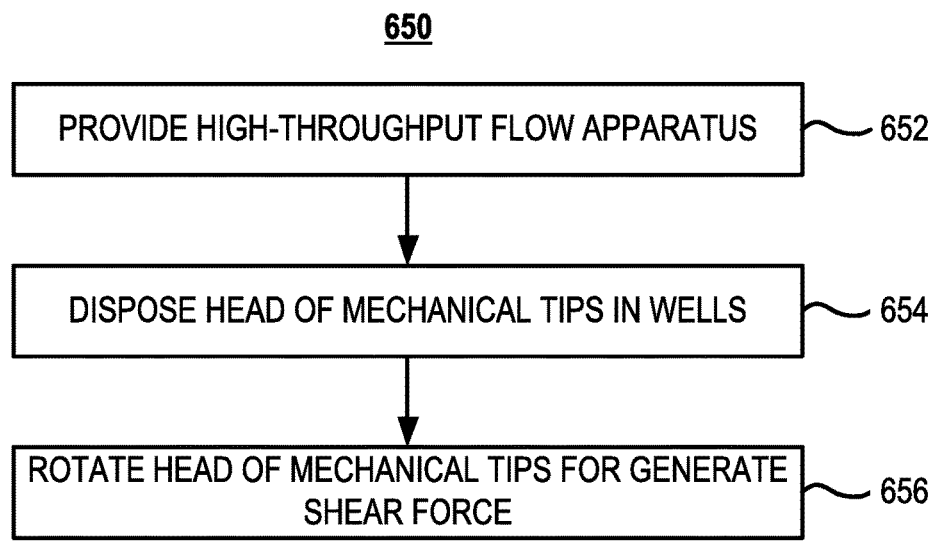
FIG. 6 illustrates an example method for applying hemodynamic waveforms to cultured cells.

FIG. 6 illustrates an example method 650 for applying hemodynamic waveforms to cultured cells. First, a high-throughput flow apparatus is provided (step 652). A head of a mechanical tip is disposed within each of the wells of the high-throughput apparatus (step 654). Each head is rotated within its corresponding well to generate a shear stress on the cells cultured within each of the wells (step 656).

As set forth above, the method 650 begins with the provision of a high-throughput flow apparatus (step 652). In some implementations, an array of wells is also provided with the high-throughput flow apparatus. The array of wells can include wells with a rounded bottom. Each tip of the high-throughput flow apparatus may be configured with a hemispheroid head. Each well of the array of wells may be at least partially filled with a liquid cell culture medium, and cells may then be grown therein as a single layer on the interior wall of each well.

Next, a head of a mechanical tip is disposed within each of the wells of the array of wells (step 654). In some implementations, the head of each of the mechanical tips is positioned a predetermined distance from the floor of well in which the head is positioned. For example, the heads may include a pinpoint standoff that maintains the predetermined distance between the head and the floor of the well or the tip may include a collar that maintains the predetermined distance. In other implementations, the heads of the high-throughput flow apparatus are allowed to contact the floor of the wells.

Finally, each head is rotated (step 656) within its corresponding well to generate a shear force through the liquid cell culture medium to the cells. For example, as the head spins within the cell culture medium, the cell culture medium also spins. In some implementations, controlling the rate at which the cell culture medium spins controls the amount of shear stress imparted on the cells. The generated shear force is substantially constant across the field of cells cultured in each of the wells. In some implementations, the cells are any type of mechano-responsive cells, such as, for example, endothelial cells and/or stem cells.

Figure 7:
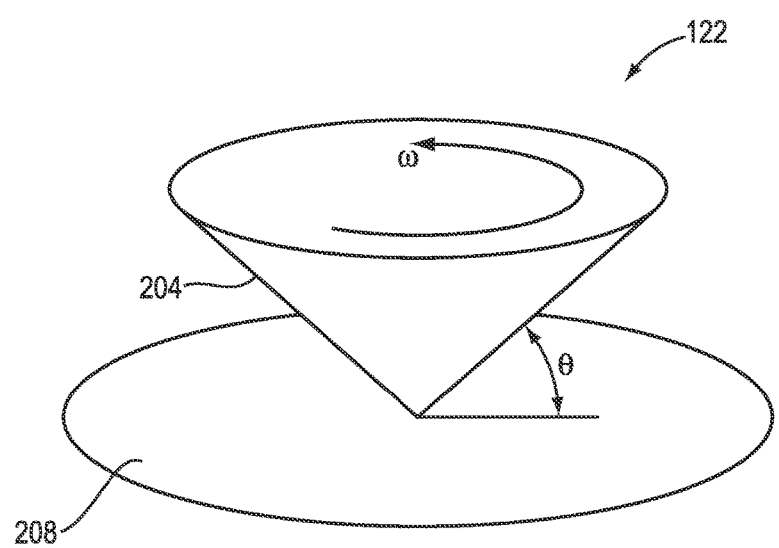
FIG. 7 schematically illustrates an example simplified head-plate shear machine.

With reference now to FIG. 7, a head-and-plate shear machine 200 has been used to apply hemodynamic waveforms to cultured human endothelial cells in the context of several specific experimental goals. The head 204 machine 200 is conical and the endothelial cells are cultured in a flat bottomed dish. With this geometry, the shear is constant over the surface of a flat bottomed dish 208, and the magnitude τ of this shear may calculated according to the equation:

$$\tau = \frac{\mu \Omega}{\tan \theta}$$

where μ is the viscosity of the fluid in the flat bottomed dish 208, Ω is the rotational speed of the head 204, and θ is the angle between the head 204 and the dish 208, as illustrated in FIG. 7. The above equation can also be used to calculate the magnitude T of shear generated by a hemi-spheroid head rotating in a well with a hemi-spherical bottom.

In some implementations, the devices described herein impart shear stress patterns having magnitudes between about 1 dynes/cm$^2$ and about 35 dynes/cm$^2$, between about 5 dynes/cm$^2$ and about 25 dynes/cm$^2$, or between about 10 dynes/cm$^2$ and about 20 dynes/cm$^2$. The equation above shows that delivering high shear requires low angle θ and high rotational speed Ω. In various implementations, to avoid scraping the well surface or attached cells (and thereby slowing the rotational speed Ω of the tip 108), the tip 108 of the MSM is designed so that it does not contact the interior surface of the well 104. For example, with reference to FIG. 3, a center 148 of the bottom surface of the rotatable head 124 may in fact be flat, while the rest of the head's bottom surface has a conical shape. In other implementations, the tip 108 does contact the surface of its corresponding well 104, or a different tip 108 shape is employed.

The analytical expression for shear in the above equation assumes a perfect head 204, and, thus, this expression is generally imprecise for the implementation of the MSM design depicted in FIG. 3. Instead, to calculate exact shear distributions in the MSM 122, a numerical method may be employed. As an example, a numerical simulation of the fluid shear forces resulting from rotation of the tip 108 having the shape depicted in FIG. 3 has been performed. The simulation results confirmed that a constant shear of approximately 35 dynes/cm$^2$ may be delivered over the majority of the well 104 surface with a head 124 angle θ of approximately 10° and a rotational speed Ω for the head of approximately 35 rotations/sec.

One motor 128 that can deliver this rotational speed, and is sufficiently small to be arrayed over a well plate as dense as the common 96-well system manufactured by Nunc, is the Arsape AM-0820 high-precision micro-stepper motor available from MicroMo Electronics, Inc. of Clearwater, Fla. This motor has a step resolution of 18 degrees, with the capability to divide each step into 256 sub-steps. In addition, the drag force of the fluid 144 on the head 124 at the head's maximum speed is within the torque specifications of the Arsape motor, meaning that the Arsape motor is also able to deliver adequate torque. Optionally, other commercially available variable-speed precision motors, or combinations thereof, may be employed instead of, or in combination with, the Arsape motor.

Ordinarily, the distance between the head 124 and the well 104 surface is tightly controlled in order to precisely deliver the desired hemodynamic shear values. A simulation has also been performed to investigate the allowable error in the height of the tip 108. The graph 300 of FIG. 8 depicts the shear distribution across the well 104 surface given a 100 μm desired height offset, and the subsequent shear distributions given errors in either direction. As can be seen, a vertical error of up to 40 μm above the desired offset gives a constant level of shear over the majority of the well 104, with a—10% error in the magnitude. Advantageously, the Arsape motor possesses precision bearings, specifying a sub-micron axial error, and accordingly does not introduce any significant error in applied shear.

Figure 9:
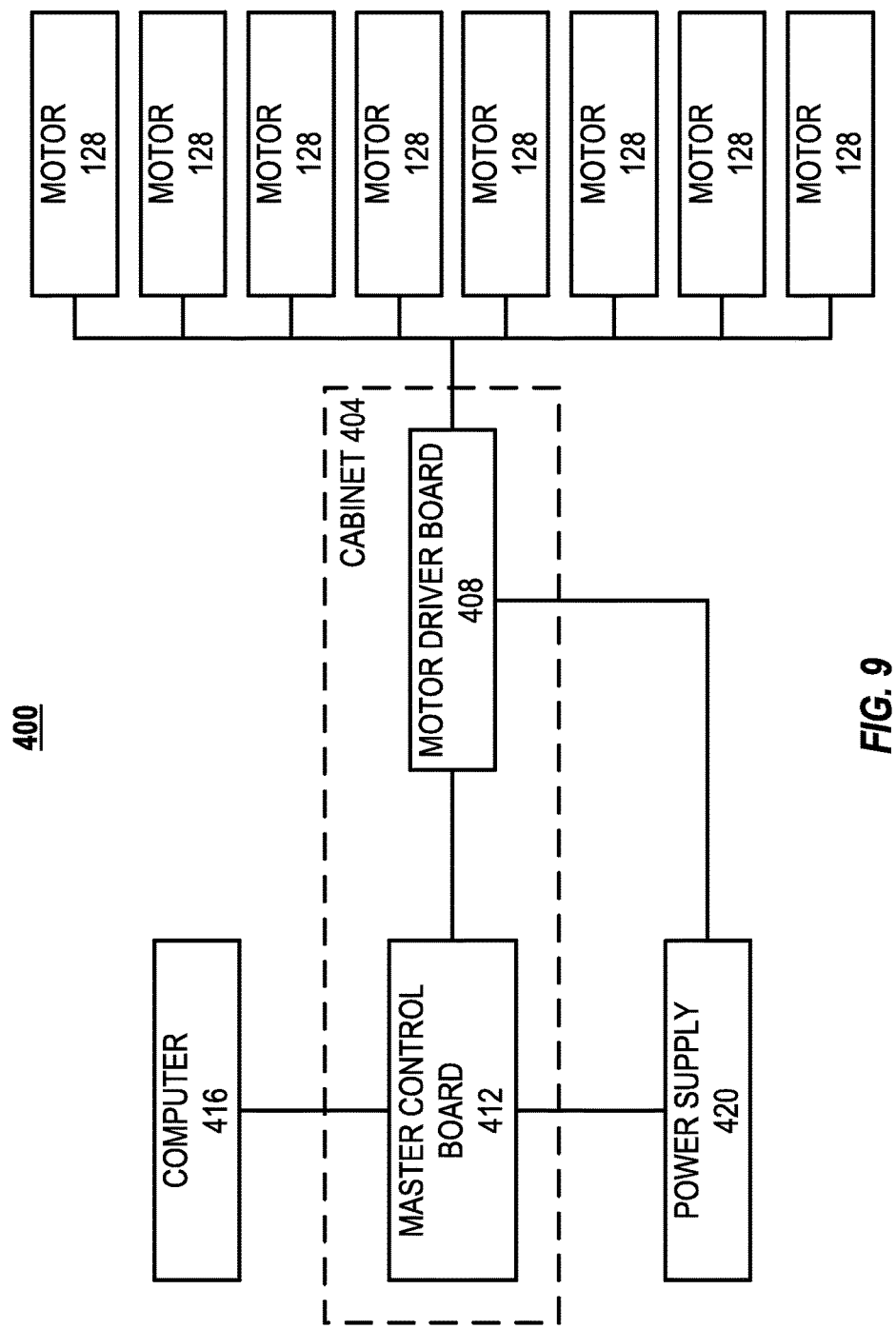
FIG. 9 illustrates example electronics for the high-throughput flow system of FIG. 1.

FIG. 9 depicts one implementation of the electronics 400 for the high-throughput flow system 100. Of course, other electronic control layouts and strategies are possible, and the layout depicted in FIG. 9 is thus provided by way of example only and is non-limiting. As depicted, the electronics 400 include circuitry, hardware, and software for driving each of the MSM 122 motors 128 with specific velocity profiles. In one implementation, a single electronics cabinet 404 houses two main components: i) an 8-channel motor driver board 408, capable of driving up to eight motors 128 with, for example, A3967 microstepping drivers manufactured by Allegro MicroSystems, Inc. of Worcester, Mass.; and ii) a master control board 412 that commands the motor driver board 408 and that interfaces with a computer 416 (e.g., a personal computer) via, for example, an RS-232 serial port. Each of the motors 128 may be coupled to a plurality of tips by, for example, a drive belt. Each motor 128 drives the corresponding drive belt which in turn rotates each of the tips coupled to the drive belt. For example and referring to FIG. 5A, for a 96 well array, each motor 128 can drive a drive belt 518, which is connected to the gear 516 atop each of the twelve tips 502 in the row of tips 502 driven by each given motor 128. In some implementations, the electronics 400 can include a stacked series of 8-channel motor driver boards 408, such that each tip can be driven directly by an independent motor 128.

Control lines running from the master control board 412 to each motor driver board 408 may also be enclosed within the electronics cabinet 404 and carry standard registered jack ("RJ") connectors. RJ connectors may also be used as the output interfaces from the 8-channel motor driver boards 408 to the eight motors 128 they drive. As such, for an exemplary 96-well system, 96 RJ inputs appear on the outside of the electronics cabinet 404—one RJ input for each motor 128 wire.

In one implementation, the master control board 412 is equipped with a PIC microcontroller manufactured by Microchip Technology, Inc. of Chandler, Ariz., enabling the master control board 412 to store various velocity profiles that may be loaded into it from, for example, the computer 416. The full motor driver system 400 may be stand-alone, and after programming the master control board 412 with the velocity profiles, the master control board may be disengaged from the computer 416 to autonomously run the motors 128 with start, stop, and pause commands. Finally, an external power supply (e.g., a 12V DC power supply, such as the VPM-S300 manufactured by V-Infinity of Tualatin, Oreg.) may be used to power the electronics 400.

Figure 10:
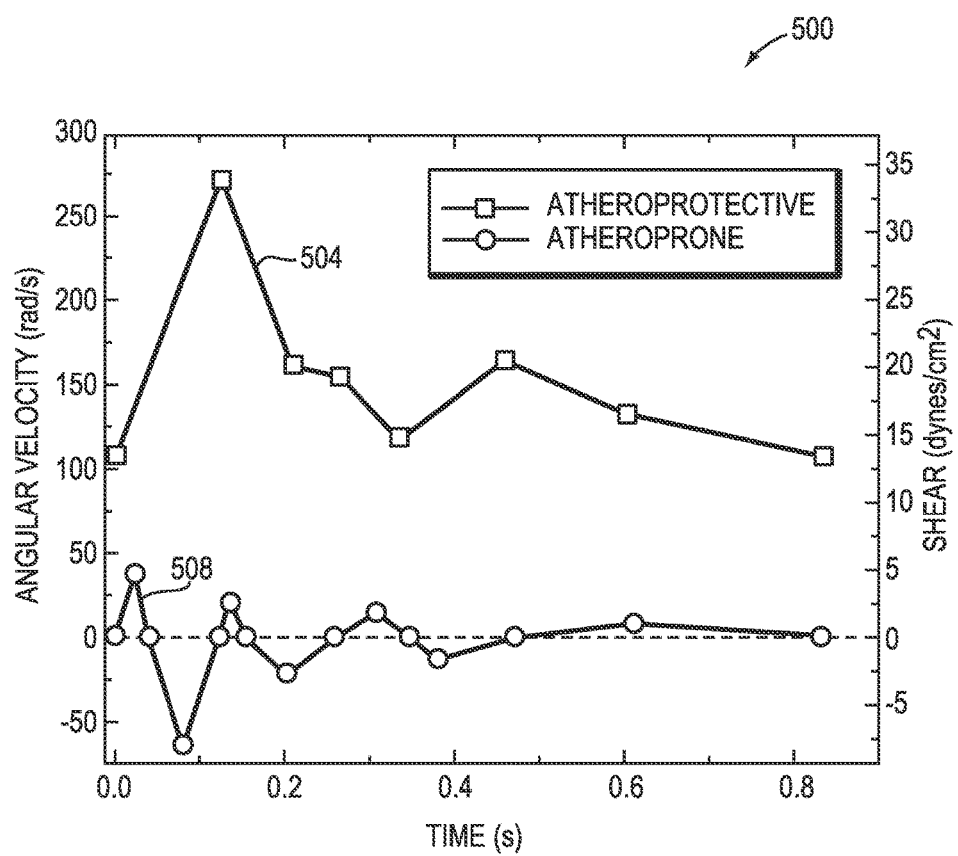
FIG. 10 illustrates a graph of example atheroprotective and atheroprone shear stress waveforms.

Any type of waveform, for example any physiological hemodynamic waveform that is capable of influencing cell behavior along different directions and/or any other arbitrarily derived waveform, may be loaded into the master control board 412. Exemplary shear profiles that may be loaded into the master control board 412 include, but are not limited to: i) an atheroprotective waveform; ii) an atheroprone waveform; iii) a constant 12 dynes/cm$^2$ waveform; iv) a constant 5 dynes/cm$^2$ waveform; v) an arbitrarily-oscillatory waveform; vi) a waveform having a pseudo-static profile consisting of a single motor step every 30 seconds; and vii) a waveform that increases stem cell differentiation. Atheroprotective and atheroprone waveforms are shear stress patterns that are representative of atherosclerosis-resistant and atherosclerosis-susceptible regions in the human carotid artery, respectively. FIG. 10 is a graph 500 depicting the discretized forms of a single cycle of an atheroprotective profile 504 and an atheroprone profile 508. The discretized, angular velocity time points may be programmed into the master control board 412.

Generally, cell culture should be performed in an environment where carbon dioxide, temperature, and humidity are all tightly regulated. Accordingly, in one implementation, with reference again to FIG. 2, carbon dioxide is pumped into the environment surrounding the array of wells 104 along a line 152 from an external source using, for example, a mixed air pressurized tank and flow regulator available from Airgas, Inc. of Radnor, Pa. In addition, the temperature and humidity in the environment surrounding the array of wells 104 may be controlled by, for example, positioning the well plate within a temperature-controlled fluid bath 156 that is isolated from the outside environment. Lexan walls may form the outer case of the fluid bath 156. In one implementation, the fluid bath 156 is heated with a heater 160, such as a 5×6 inch 2.5 Watt/in$^2$ flexible silicone fiberglass insulated heater (e.g., Part # SRFG available from Omega Engineering, Inc. of Stamford, Conn.). The temperature of the heater 160 may be controlled by using a feedback loop that includes temperature measurement with a thermocouple 164 (e.g., Part # KMTSS-040U-6 available from Omega Engineering, Inc. of Stamford, Conn.), and heater input power adjustment with a ramp/soak temperature controller (e.g., Part # CN74030 available from Omega Engineering, Inc. of Stamford, Conn.). The temperature of the fluid bath 156 may be set in order to maintain a temperature of, for example, approximately 37° C. in each well 104.

In one implementation, the evaporation rate in the fluid bath 156 is about 80 ml/hr/cm$^2$. At this rate, the fluid bath 156 can be employed for approximately 24 hours before its fluid level drops to a point where it is no longer contacting the well plate. In case this duration is not long enough, the fluid bath 156 may also include a connection 168 to an external fluid source so that the fluid level within the fluid bath 156 can be adjusted without having to open the high-throughput flow system 100.

As will be appreciated by one of ordinary skill in the art, several alternatives exist for controlling the environment within the wells 104. For example, air temperature and humidity may be controlled in a separate device and then be pumped into the environment surrounding the array of wells 104, while the temperature of individual wells 104 can be controlled by applying heat sources directly to the well plate. Alternatively, an enclosure for the entire high-throughput flow system 100 may be used to control both the temperature and humidity.

The high-throughput flow system 100 may be operated to generate a variety of different flow conditions (e.g., both healthy flow conditions and diseased flow conditions) and the behavior of different types of mechano-responsive cells (e.g., endothelial, stem, etc.) may be investigated under those different flow conditions. Moreover, candidate drugs, small molecules, siRNAs, shRNAs, microRNAs, and/or genes may be introduced to the cells to test their efficacy in treating certain diseased flow conditions. For example, high-throughput screens may be employed to identify, without limitation: i) genes (e.g., via cDNA libraries, shRNA libraries, siRNA libraries, microRNAs, etc.) and/or small molecules that are capable of conferring vascular atheroprotection, and might thus be used for the treatment of atherosclerosis and/or other inflammatory diseases; ii) genes (e.g., via cDNA libraries, shRNA libraries, siRNA libraries, microRNAs, etc.) and/or small molecules that are capable of inhibiting the expression of atherosclerosis-susceptible genes, and might thus be used for the treatment of atherosclerosis and/or other inflammatory diseases; iii) genes (e.g., via cDNA libraries, shRNA libraries, siRNA libraries, microRNAs, etc.) and/or small molecules that are capable of increasing the differentiation of embryonic stem cells into blood components, and might thus be used in the treatment of hematopoietic disorders; iv) genes (e.g., via cDNA libraries, shRNA libraries, siRNA libraries, microRNAs, etc.) and/or small molecules that are capable of regulating cellular differentiation (e.g., epithelial, osteoclast, osteoblasts, and cardiac myocytes); and v) small molecules that are capable of disrupting vascular function and/or inducing endothelial toxicity, and might thus be used for assessing drug toxicity specific to the vascular endothelium with implications for other systems or organs.

The large-scale, high-throughput parallel-processing flow system 100 enables the direct comparison between and among a large number of cell populations at the same time, and therefore reduces the time needed to obtain such high-throughput screening data on drug discovery, drug safety, and other applications.

EXAMPLES

Figure 11A:
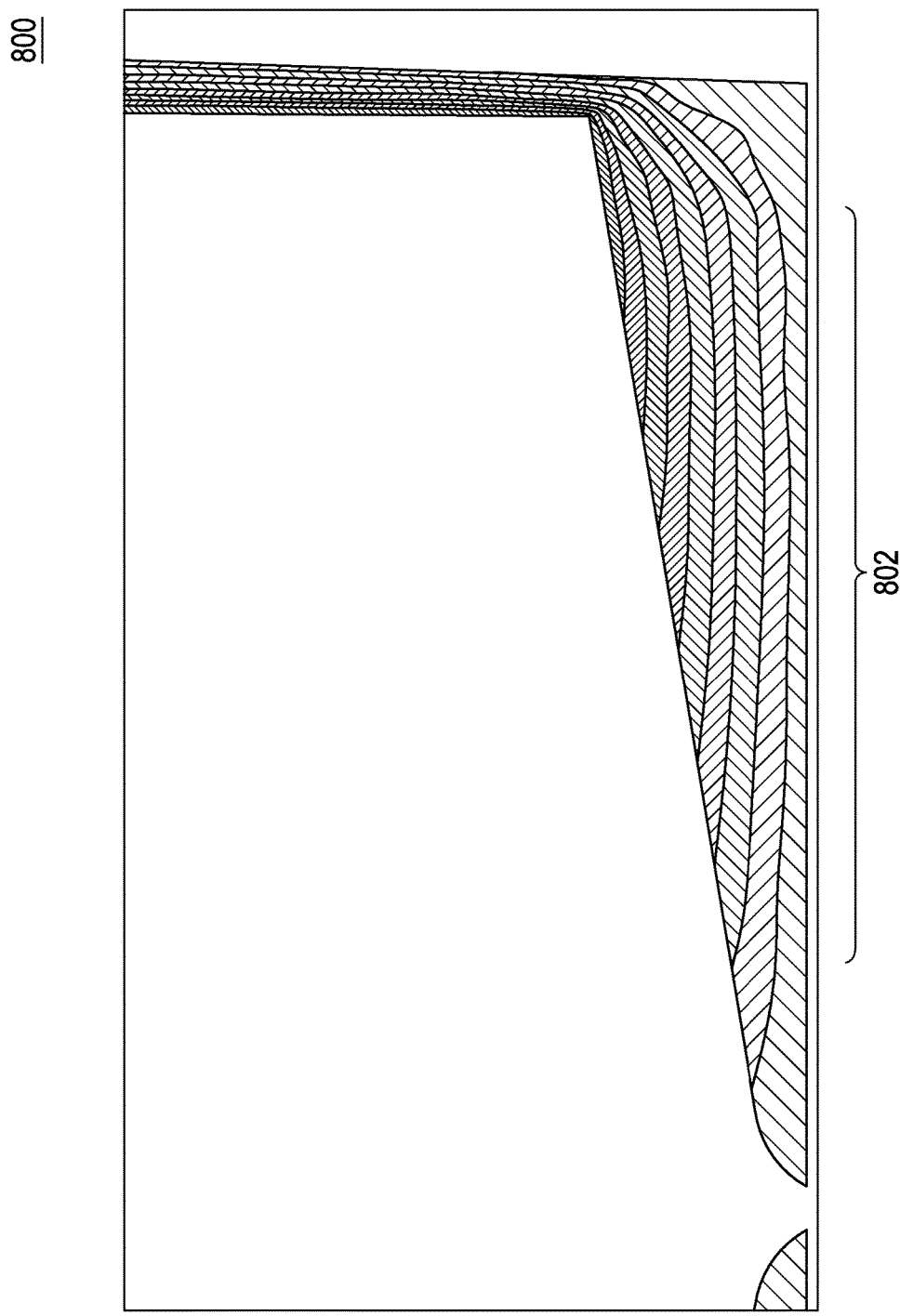

FIGS. 11A-11C illustrate simulated velocity profiles generated in wells using mechanical tips with different shaped heads. FIG. 13A illustrates a simulated velocity profile 800 for a conical shaped head in a flat bottomed well. When rotating at a constant rate, the head generates a constant shear stress within a region 802. As illustrated, outside of the region 802 the velocity profile 800 is no longer constant, resulting in a different imparted shear stress. FIG. 13B illustrates a simulated velocity profile 810 generated by a hemi-spherical shaped head. FIG. 13C illustrates a simulated velocity profile 820 generated by a hemi-spheroid shaped head (e.g., a head with a semi-vesica piscis cross-sectional shape). As illustrated, both the hemi-spherical and hemi-spheroid shaped heads generated a substantially constant velocity (and shear stress) across the wall of the well. However, the hemi-spheroid shaped head generated a velocity profile 820 wherein the width of the layers of the velocity profile are more uniform when compared to the velocity profile 810 generated with the hemi-spherical head.

Figure 12:
FIG. 12 illustrates a graph of the level of KLF2 mRNA gene expression induced in cells under two different flow conditions using a high-throughput flow system similar to the system illustrated in FIG. 1.

FIG. 12 illustrates a graph 900 of the level of KLF2 mRNA gene expression induced in cells under two different flow conditions using a high-throughput flow system similar to the system illustrated in FIG. 1. In the experiments conducted to test KLF2 mRNA gene expression, endothelial cells were plated in the rounded-bottom wells of a 96 well plate. The well plate was placed in a high-throughput flow system. The tips of the system were lowered into corresponding wells. The system included tips with hemispheroid heads similar to the tips described in relation to FIGS. 5A-5E. After a recovery period, the cells were subjected to an atheroprotective waveform for 24 hours. Control endothelial cells ("static cells") were plated in a similar fashion, but were not exposed to an atheroprotective waveform. The graph 900 illustrates that cells exposed to the atheroprotective waveform experience about a 6-fold increase in KLF2 mRNA gene expression when compared to cells cultured in a static well. The increase in KLF2 mRNA gene expression demonstrates that the system described herein, with a hemispheroid shaped head, effectively evokes cellular responses similar to the cellular responses seen in in vivo conditions.

While the disclosure has been particularly shown and described with reference to specific implementations, it will be understood by those skilled in the art that various changes in form and detail may be made therein without departing from the spirit and scope of the disclosure as defined by the appended claims. The scope of the disclosure is thus indicated by the appended claims and all changes that come within the meaning and range of equivalency of the claims are therefore intended to be embraced.

What is claimed:

1. A system for inducing shear within an array of wells, the system comprising:
   a plurality of mechanical tips configured in a horizontally planar array, each mechanical tip corresponding to a different well of the array of wells, each mechanical tip comprising a head and a pinpoint standoff extending along a central axis of the head and configured to maintain a predetermined distance between a floor of the head and a floor of its corresponding well; and
   a motor associated with at least one of plurality of mechanical tips, the motor configured to drive the at least one of the plurality of mechanical tips to impart a shear stress pattern in the well corresponding to the at least one of the plurality of mechanical tips.

2. The system of claim 1, wherein each head has a hemispheroid shape.

3. The system of claim 2, wherein the hemispheroid shape is defined by two adjacent arcs, wherein a center of each of the adjacent arcs is a predetermined distance from the central axis of the head.

4. The system of claim 2, wherein the hemispheroid shape forms a point about which the head of each of the plurality of mechanical tips rotates.

5. The system of claim 2, wherein the hemispheroid shape has a semi-circular cross-sectional shape.

6. The system of claim 2, further comprising the array of wells, wherein each well of the array of wells have a hemi-spherical bottom.

7. The system of claim 1, wherein each of the plurality of mechanical tips further comprise a groove that enables the mechanical tip to move vertically relative to the motor.

8. A method comprising:
   providing a system for inducing shear and an array of hemi-spherical bottomed wells, the system for inducing shear comprises:
   a plurality of mechanical tips configured in a horizontally planar array, each mechanical tip corresponding to a different well of the array of wells, each mechanical tip comprising a head and a pinpoint standoff extending along a central axis of the head and configured to maintain a predetermined distance between a floor of the head and a floor of its corresponding well; and
   at least one motor associated with the plurality of mechanical tips;
   disposing the head of each of the plurality of mechanical tips into each well of the array of wells; and
   rotating the head of each of the plurality of mechanical tips with the at least one motor to generate a shear force within the each well of the array of wells.

9. The method of claim 8, further comprising culturing a field of cells in each well of the array of wells.

10. The method of claim 9, wherein the shear force is substantially constant across the field of cells in each well of the array of wells.

11. The method of claim 8, wherein each has a hemispheroid shape.

12. The method of claim 11, wherein the hemispheroid is defined by two adjacent arcs, wherein a center of each of the adjacent arcs is a predetermined distance from the central axis of the head.

13. The method of claim 11, wherein the hemispheroid shape forms a point about which the head of each of the plurality of mechanical tips rotates.

14. The method of claim 11, wherein the hemispheroid shape has a semi-circular cross-sectional shape.

* * * * *